(12) United States Patent
Suffin

(10) Patent No.: US 10,325,067 B1
(45) Date of Patent: Jun. 18, 2019

(54) STATISTICAL QUALITY CONTROL OF MEDICAL LABORATORY RESULTS

(71) Applicant: Quest Diagnostics Investments Inc., Wilmington, DE (US)

(72) Inventor: Stephen Suffin, Madison, NJ (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 549 days.

(21) Appl. No.: 13/731,784

(22) Filed: Dec. 31, 2012

Related U.S. Application Data

(60) Provisional application No. 61/582,293, filed on Dec. 31, 2011.

(51) Int. Cl.
| | |
|---|---|
| *G16H 10/00* | (2018.01) |
| *G06F 19/00* | (2018.01) |
| *G16H 15/00* | (2018.01) |
| *G16H 10/40* | (2018.01) |
| *G16H 10/60* | (2018.01) |

(52) U.S. Cl.
CPC .............. *G06F 19/32* (2013.01); *G16H 10/00* (2018.01); *G16H 10/40* (2018.01); *G16H 10/60* (2018.01); *G16H 15/00* (2018.01)

(58) Field of Classification Search
CPC .... G06F 19/345; G06F 19/3487; G06F 19/36; G06F 19/366; G06F 19/30; G06F 19/32; G06F 19/321; G06F 19/325; G06F 19/326; G06F 19/3431; G06F 19/363; G06F 17/00; G06F 17/278; G06F 17/30032; G06F 17/30979; G06F 17/30994; G06F 17/30997; G06F 17/40; G06F 19/322; G06F 19/3406; G06F 19/3418; G16H 10/00; G16H 10/40; G16H 10/60; G16H 15/00
USPC ......................................................... 702/19
See application file for complete search history.

(56) References Cited

U.S. PATENT DOCUMENTS

| | | | |
|---|---|---|---|
| 2006/0173663 A1* | 8/2006 | Langheier et al. | ............. 703/11 |
| 2007/0198213 A1* | 8/2007 | Parvin | ................... G06F 19/366 702/179 |

* cited by examiner

*Primary Examiner* — Sujoy K Kundu
*Assistant Examiner* — Lynda Dinh
(74) *Attorney, Agent, or Firm* — Jon E. Gordon; Haug Partners LLP

(57) ABSTRACT

Laboratory testing plays a significant and growing role in the delivery of medical services. Fresh analysis of past test results has led to discovery of previously unknown correlations between statistical properties of analyte values and parameters such as age, sex, and region. Observed values in patient populations have also newly been discovered to show both secular and regular periodic variations over time. Embodiments of the invention may use information about these correlations to improve quality control and other statistical analysis of patient samples by applying adjusted reference ranges to quality control methodologies, and providing a quality control grade for patient samples based on the adjusted reference ranges.

8 Claims, 4 Drawing Sheets

STATISTICAL QUALITY CONTROL OF MEDICAL LABORATORY RESULTS

CROSS-REFERENCE TO RELATED APPLICATION

This application claims priority of U.S. Provisional Application Ser. No. 61/582,293, filed 31 Dec. 2011, which is incorporated by reference herein, including without limitation all appendices thereto.

This application is related to provisional U.S. patent application No. 61/254,652, filed 23 Oct. 2009 and titled "Systems and Methods for Quality Assurance in Providing Laboratory Services", and to U.S. patent application Ser. No. 12/911,106, filed 25 Oct. 2010 and titled "Systems and Methods for Quality Assurance in Providing Laboratory Services", both of which are incorporated fully (including all appendices thereto) herein by reference. This application is also related to provisional U.S. patent application no. 61/429,102, filed 31 Dec. 2010 and titled "Delivery of Medical Services Based on Observed Parametric Variation in Analyte Values", and to U.S. patent application Ser. No. 13/341,081, filed 30 Dec. 2010 and titled "Delivery of Medical Services Based on Observed Parametric Variation in Analyte Values", both of which are incorporated fully (including all appendices thereto) herein by reference.

COPYRIGHT NOTICE

A portion of the disclosure of this patent document contains material that is subject to copyright protection. The copyright owner has no objection to the facsimile reproduction by anyone of the patent document or the patent disclosure as it appears in the Patent and Trademark Office patent files or records but otherwise reserves all copyrights whatsoever.

BACKGROUND

Laboratory testing plays a significant and growing role in the delivery of medical services. Existing testing systems and methods provide reference ranges for test results, but those systems, methods, and reference ranges fail to reflect newly-observed variation in the measured values of the tested analytes.

A failure to reflect these variations is therefore also reflected, and in fact magnified, in the quality control methodologies employed by laboratories, which may comprise analysis of testing results, e.g., across a batch of tests. Such quality control methodologies therefore result in flawed quality control procedures and inefficiencies. For example, a batch of tests that are otherwise within a proper reference range, when factoring in newly-observed variations, may be improperly flagged for re-testing by a quality control process that fails to factor in the variations.

BRIEF SUMMARY OF THE INVENTION

Medical diagnosis and treatment have come to depend more and more on laboratory testing. With this increased dependence has come increased need to ensure that adequate systems and methods are in place to ensure quality control of testing processes and related persons, materials, and equipment.

Quality control methods and systems may include recording, e.g., data about persons and processes involved in testing and automatically applying rules to ensure that all applicable standards are met. Some such methods and systems are disclosed in provisional U.S. patent application No. 61/254,652 and U.S. patent application Ser. No. 12/911,106.

Additional quality control methods may comprise analysis of testing results themselves. For example, a batch of samples being analyzed may include control samples for which expected values of an analyte may be known in advance. Excessive variance from these expected values may indicate, e.g., that an entire batch needs to be retested.

Results from a batch of samples may also be compared, e.g., to a distribution of results expected from a population. Excessive disparity between the measured and expected distributions may also indicate a need for retesting.

As disclosed in provisional U.S. patent application no. 61/429,102 and U.S. patent application Ser. No. 13/341,081, it has been found that expected distributions of results may vary based, e.g., on time of year and patient demographics. Even a single individual's results may vary, and even predictably, based on the patient's changes in age and the time of year.

For example, fresh analysis of past test results has led to discovery of previously unknown correlations between statistical properties of analyte values and parameters such as age, sex, and region. Observed values in patient populations have also newly been discovered to show both secular and regular periodic variations over time.

Thus, according to embodiments of the invention, methods of quality control may calculate a grade for a test, or batch of tests, based on the expected distribution of test results for samples in the batch, factoring in these variations. Such expected distribution may be based on expected parametric variations in individual results, results in one or more sub-populations, or both. A method according to an embodiment of the invention may also include transmitting an indication that tests need to be done again on one or more samples, and/or indicating that one or more results may be released based on the grade.

According to an embodiment of the invention, a computer system for providing a quality control grade comprises one or more processors and one or more computer-readable storage media encoded with instructions that, when executed by at least one of the processors, cause the computer system to at least to carry out a method of calculating the quality-control grade. The method comprises retrieving at least one reference range value reflecting at least one time-periodic function based on a plurality of results of a medical test performed at a plurality of times upon a plurality of members of a population. The method also comprises applying the reference range based at least on the time-periodic function to at least one patient sample and calculating a quality control grade based on the applied reference range.

In embodiments of the invention, some or all steps of some or all of the above-described methods may be performed by or in connection with one or more computer systems. Such a computer system, according to an embodiment of the invention, may include one or more processors, one or more interfaces operatively coupled to at least one of the processors, one or more databases, and/or one or more computer-readable storage media.

Embodiments of the invention also include computer systems programmed to carry out the above-described methods and computer-readable storage media encoded with instructions that, when executed by one or more processors within a computer system, cause the computer system to carry out the above-described methods.

DETAILED DESCRIPTION OF PREFERRED EMBODIMENTS

Figure 1:
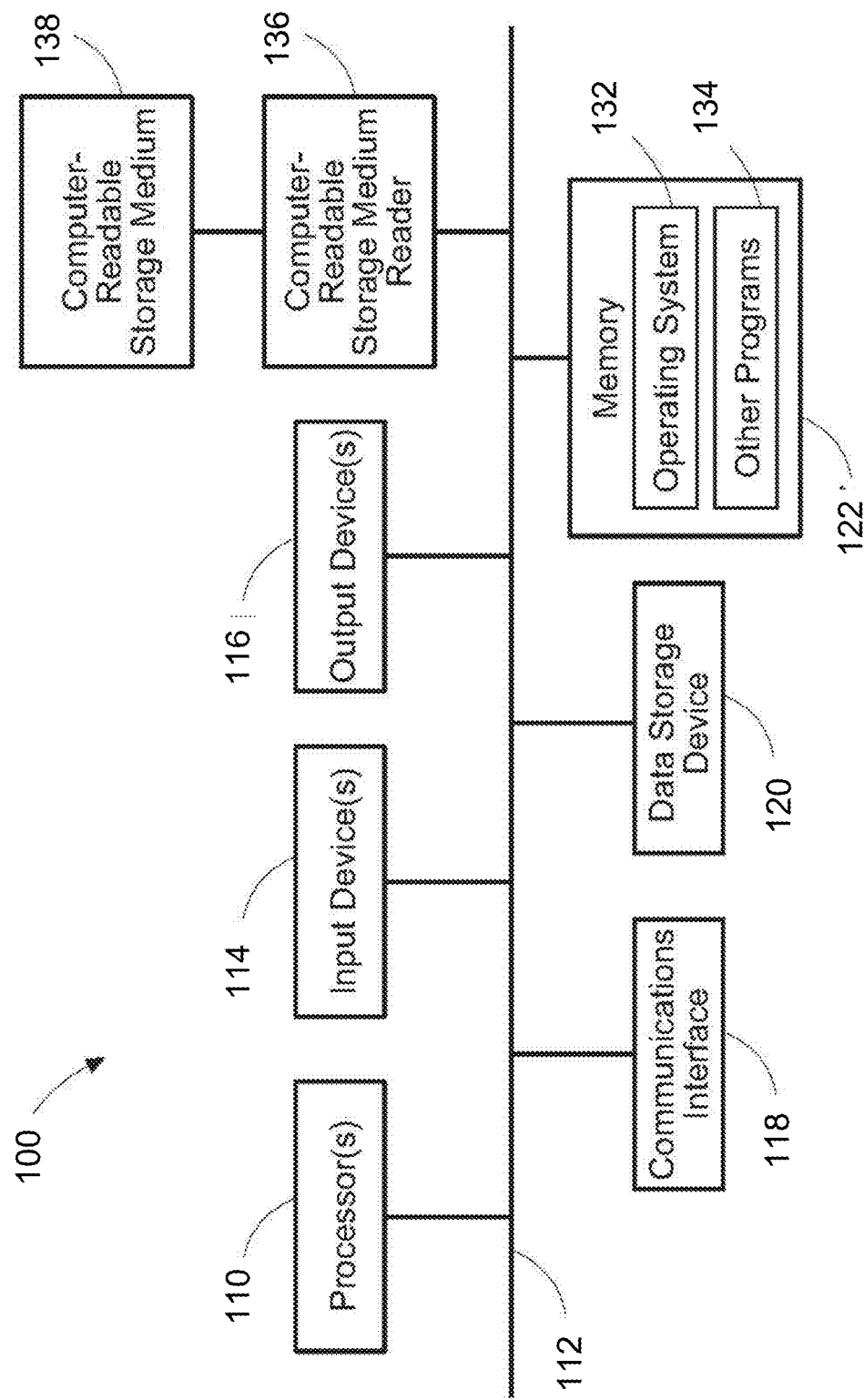
FIG. 1 is a block diagram depicting an exemplary computer system with which embodiments of the invention may at least partially be implemented.

Embodiments of the invention may be implemented by systems using one or more programmable digital computers. FIG. 1 depicts an example of one such computer system 100, which includes at least one processor 110, such as, e.g., an Intel or Advanced Micro Devices microprocessor, coupled to a communications channel or bus 112. The computer system 100 further includes at least one input device 114 such as, e.g., a keyboard, mouse, touch pad or screen, or other selection or pointing device, at least one output device 116 such as, e.g., an electronic display device, at least one communications interface 118, at least one data storage device 120 such as a magnetic disk or an optical disk, and memory 122 such as ROM and RAM, each coupled to the communications channel 112. The communications interface 118 may be coupled to a network (not depicted) such as the Internet.

Although the computer system 100 is shown in FIG. 1 to have only a single communications channel 112, a person skilled in the relevant arts will recognize that a computer system may have multiple channels (not depicted), including for example one or more busses, and that such channels may be interconnected, e.g., by one or more bridges. In such a configuration, components depicted in FIG. 1 as connected by a single channel 112 may interoperate, and may thereby be considered to be coupled to one another, despite being directly connected to different communications channels.

One skilled in the art will recognize that, although the data storage device 120 and memory 122 are depicted as different units, the data storage device 120 and memory 122 can be parts of the same unit or units, and that the functions of one can be shared in whole or in part by the other, e.g., as RAM disks, virtual memory, etc. It will also be appreciated that any particular computer may have multiple components of a given type, e.g., processors 110, input devices 114, communications interfaces 118, etc.

The data storage device 120 (FIG. 1) and/or memory 122 may store instructions executable by one or more processors or kinds of processors 110, data, or both. Some groups of instructions, possibly grouped with data, may make up one or more programs, which may include an operating system 132 such as Microsoft Windows®, Linux®, Mac OS®, or Unix®. Other programs 134 may be stored instead of or in addition to the operating system. It will be appreciated that a computer system may also be implemented on platforms and operating systems other than those mentioned. Any operating system 132 or other program 134, or any part of either, may be written using one or more programming languages such as, e.g., Java®, C, C++, C#, Visual Basic®, VB.NET®, Perl, Ruby, Python, or other programming languages, possibly using object oriented design and/or coding techniques.

One skilled in the art will recognize that the computer system 100 (FIG. 1) may also include additional components and/or systems, such as network connections, additional memory, additional processors, network interfaces, input/output busses, for example. One skilled in the art will also recognize that the programs and data may be received by and stored in the system in alternative ways. For example, a computer-readable storage medium (CRSM) reader 136, such as, e.g., a magnetic disk drive, magneto-optical drive, optical disk drive, or flash drive, may be coupled to the communications channel 112 for reading from a CRSM 138 such as, e.g., a magnetic disk, a magneto-optical disk, an optical disk, or flash RAM. Alternatively, one or more CRSM readers may be coupled to the rest of the computer system 100, e.g., through a network interface (not depicted) or a communications interface 118. In any such configuration, however, the computer system 100 may receive programs and/or data via the CRSM reader 136. Further, it will be appreciated that the term "memory" herein is intended to include various types of suitable data storage media, whether permanent or temporary, including among other things the data storage device 120, the memory 122, and the CSRM 138.

Figure 2:
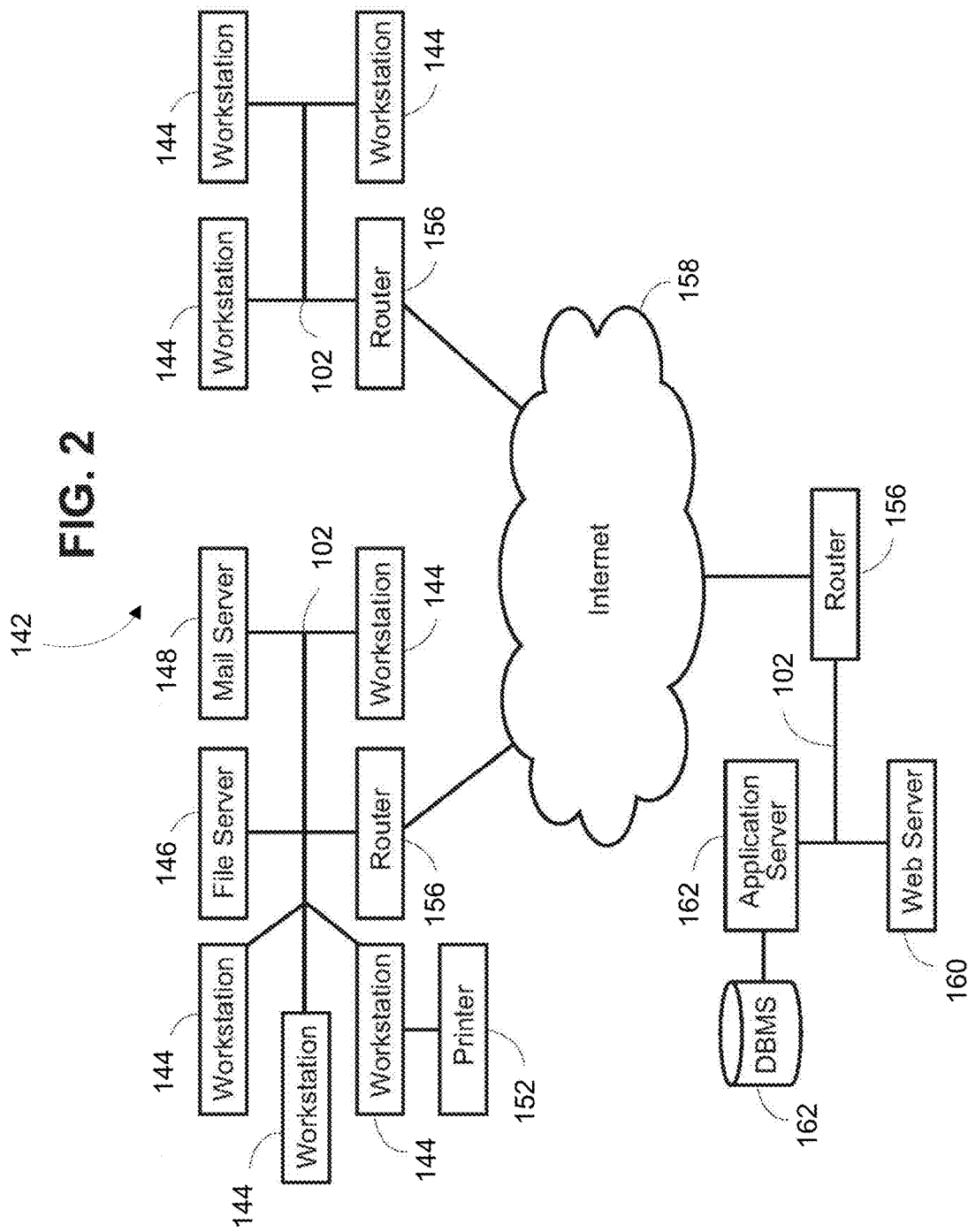
FIG. 2 is a block diagram depicting an exemplary interconnected network with which embodiments of the invention may at least partially be implemented.

Two or more computer systems 100 (FIG. 1) may communicate, e.g., in one or more networks, via, e.g., their respective communications interfaces 118 and/or network interfaces (not depicted). FIG. 2 is a block diagram depicting an example of one such interconnected network 142. Network 142 may, for example, connect one or more workstations 144 with each other and with other computer systems, such as file servers 146 or mail servers 148. A workstation 144 may comprise a computer system 100. The connection may be achieved tangibly, e.g., via Ethernet® or optical cables, or wirelessly, e.g., through use of modulated microwave signals according to the IEEE 802.11 family of standards. A computer workstation 144 or system 100 that participates in the network may send data to another computer workstation system in the network via the network connection.

One use of a network 142 (FIG. 2) is to enable a computer system to provide services to other computer systems, consume services provided by other computer systems, or both. For example, a file server 146 may provide common storage of files for one or more of the workstations 144 on a network 142. A workstation 144 sends data including a request for a file to the file server 146 via the network 142 and the file server 146 may respond by sending the data from the file back to the requesting workstation 144.

Further, a computer system may simultaneously act as a workstation, a server, and/or a client. For example, as depicted in FIG. 2, a workstation 144 is connected to a printer 152. That workstation 144 may allow users of other workstations on the network 142 to use the printer 152, thereby acting as a print server. At the same time, however, a user may be working at the workstation 144 on a document that is stored on the file server 146.

The network 142 (FIG. 2) may be connected to one or more other networks, e.g., via a router 156. A router 156 may also act as a firewall, monitoring and/or restricting the flow of data to and/or from the network 142 as configured to protect the network. A firewall may alternatively be a separate device (not pictured) from the router 156.

An internet may comprise a network of networks 142 (FIG. 2). The term "the Internet" refers to the worldwide network of interconnected, packet-switched data networks that uses the Internet Protocol (IP) to route and transfer data. In the example depicted in FIG. 3, the Internet 158 provides a communications network over which computer systems in network 142 communicate. For example, a client and server on different networks may communicate via the Internet 158, e.g., a workstation 144 may request a World Wide Web document from a Web Server 160. The Web Server 160 may process the request and pass it to, e.g., an Application Server 162. The Application Server 162 may then conduct further processing, which may include, for example, sending data to and/or receiving data from one or more other data sources. Such a data source may include, e.g., other servers on the same computer system 100 or LAN 102, or a different computer system or LAN and/or a Database Management System ("DBMS") 162.

As will be recognized by those skilled in the relevant art, the terms "workstation," "client," and "server" are used herein to describe a computer's function in a particular context. A workstation may, for example, be a computer that one or more users work with directly, e.g., through a keyboard and monitor directly coupled to the computer system. A computer system that requests a service through a network is often referred to as a client, and a computer system that provides a service is often referred to as a server. But any particular workstation may be indistinguishable in its hardware, configuration, operating system, and/or other software from a client, server, or both.

The terms "client" and "server" may describe programs and running processes instead of or in addition to their application to computer systems described above. Generally, a (software) client may consume information and/or computational services provided by a (software) server.

Figure 3:
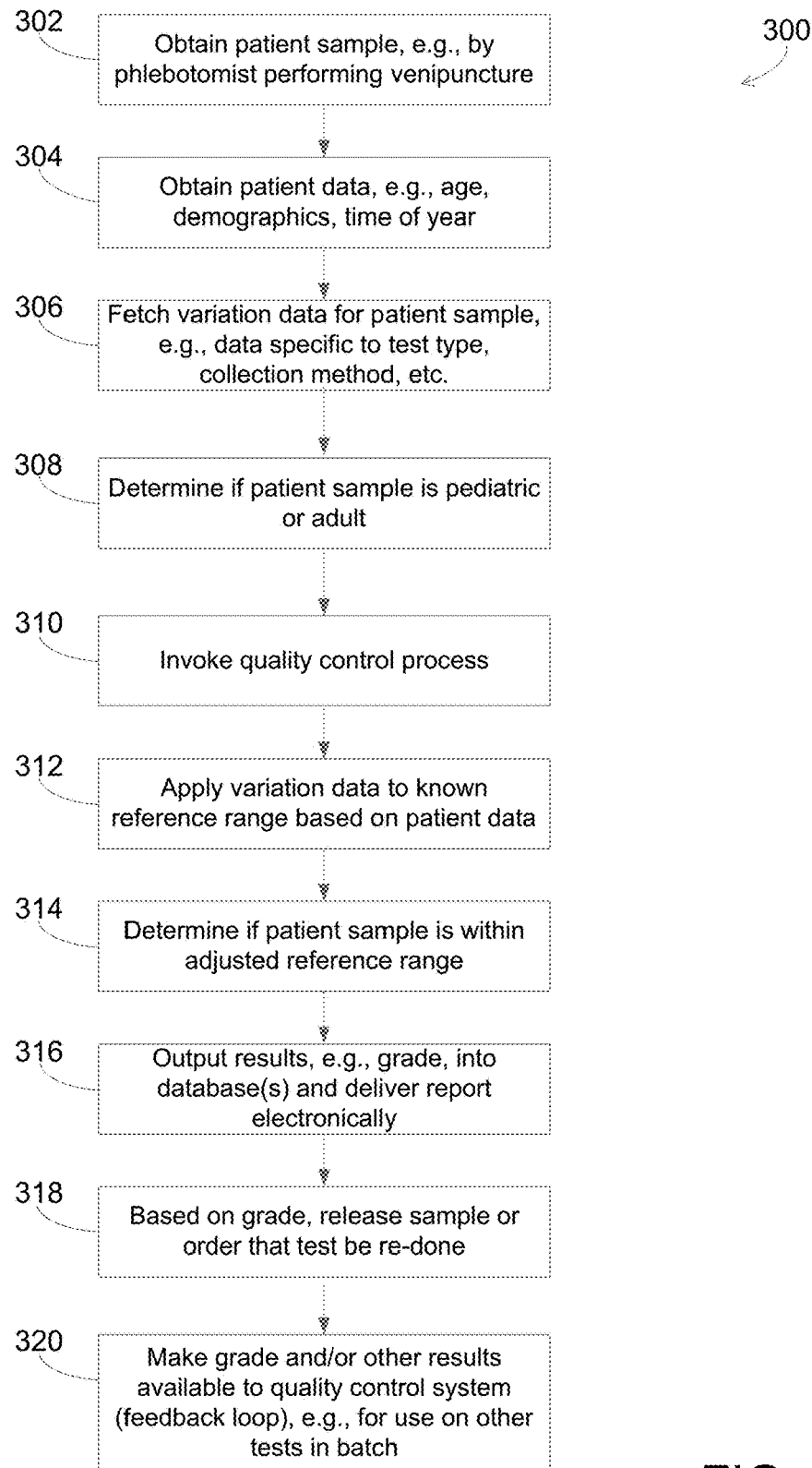
FIG. 3 is a flow diagram depicting calculation of a grade for a test or batch of tests based on the expected distribution of test results for samples in the batch, factoring in variations.

Referring to FIG. 3, in connection with embodiments of the invention, one or more computer systems, which may be interconnected, e.g., to each other and/or to other computer systems, may calculate and/or store, retrieve, manipulate, analyze, transmit, and/or receive data related to values of analytes measured, e.g., in laboratory tests. (An analyte is a substance that is being identified or is the subject of a measurement in a test. Strictly speaking, the measurement is not of an analyte itself, but, rather, is of a quantity related to that analyte, such as the concentration of that analyte in a sample being tested. For example, a test may measure the concentration of glucose in blood serum; in such a test, glucose is the analyte. Nonetheless, a common shorthand is to refer to measurement of an analyte, and the correct meaning is clear from context.)

As represented in block 302, in an embodiment, retrieving, manipulating, analyzing, transmitting, and/or receiving data related to values of analytes in laboratory tests may be enabled by first obtaining a patient sample, e.g., by a phlebotomist performing venipuncture, by acquiring a tissue sample, or by another laboratory test. The patient sample may be processed by traditional methods, or using one or more of the computer systems interconnected, as discussed herein.

In block 304, in an embodiment, the one or more computer systems may obtain patient data, e.g., age, demographics, time of year, or other information useful in measuring or analyzing analyte values. Information collected as part of block 304 may be further analyzed or manipulated before serving as inputs to other calculations or algorithms discussed herein. For example, the age value may be used to determine if a patient sample is from a pediatric or adult patient. Demographic information may be used to determine the gender or ethnicity of the patient. As discussed in more detail below, these factors may influence certain calculations or processing flows.

In block 306, in an embodiment, the one or more computer systems may fetch variation data (including, e.g., one or more reference ranges based on factors such as age, gender, time of year, etc.) related to the patient sample and/or test type and/or patient data. The variation data may be in the form of reference ranges with variation data already applied, or reference ranges with separate variation/offset data to be applied to the reference ranges.

For example, in an embodiment, if the patient sample is blood intended for a Vitamin D level test that was drawn in December in the Northeast of the United States, block 306 would fetch variation data or proper reference ranges that had been calculated for this particular combination.

More detail on the calculation processes behind the information fetched in block 306 can be found in U.S. patent applications 61/254,652, 12/911,106, 61/429,102, and 13/341,081, which are cross-referenced above. In short, as one example, statistical calculations could be the basis for the calculation of such reference ranges. For example, in an analyte whose values follow a normal distribution, for each sub-population, a separate reference range may be established, e.g., of two standard deviations (for that sub-population) around the mean (also for that sub-population). In one embodiment, the respective reference ranges may then be stored, e.g., for future reference, such as in block 306 herein. In another embodiment, offset values (as opposed to the ranges themselves, which may change) may then be stored, e.g., for future reference, such as in block 306 herein.

More specifically, analyte values measured in medical laboratory tests commonly reflect or approximate a normal or log-normal distribution. Based on this fact, a "reference range" may be established for a particular test and/or analyte. A reference range for a particular test or measurement is usually defined as the prediction interval of values that 95% (or 2 standard deviations) of the population fall into. Depending on the circumstances, the reference range may be established with regard to an entire population or only a healthy population.

Reference ranges may often—but nonetheless incorrectly—be regarded as establishing "normal" values for analytes. Not everyone manifesting a value outside the reference range is abnormal or unhealthy, however, and not everyone within the reference range is healthy or free of tested-for medical conditions. Nonetheless, reference ranges may be considered useful for diagnosis, e.g., as indicating possible avenues for follow-up; it is apparent that a value for a patient that is outside the commonly-observed range of values may in fact be abnormal and an indication that a medical condition exists.

It will therefore be appreciated that the diagnostic utility of a reference range may be highest if the range best reflects the range of expected values from the relevant population. In some cases, existing reference ranges reflect that fact. For example, the distributions of values of, e.g., estrogen, testosterone, and prostate-specific antigen (PSA), measured in men will differ from that of values measured in women, and separate reference ranges for may consequently be established for men and women.

As has been discovered through the applicants' analyses of historical test results, however, mean values and standard deviations for many analytes vary depending on the patient's age, sex, and location. Both secular and regular periodic variation based on time have also been observed. In many cases, the observed mean values over time may be fit to a curve with a high degree of correlation, with the same curve fitting to different sub-populations with variations only in the coefficients of polynomial and/or time-periodic terms in the equation.

Periodic variations may be attributed in some cases to environmental factors, in some cases to behavioral factors, and in some cases to both. For example, vitamin D levels might vary seasonally reflecting both the seasonal variation in the length and intensity of sunlight reaching the Earth's surface each day and the relative time spent indoors and outdoors, e.g., in summer versus winter. In some populations, for example, a vitamin D level of 22 ng/mL might be expected in March, but should not be seen in August.

As another example, in some populations, cholesterol levels may increase in late fall and winter, reflecting holiday indulgence, while falling in the late spring and summer as people may lose weight to look more attractive in swimsuits. In such a population, a total cholesterol level of 200 mg/dL might be expected in January but not in July.

According to embodiments of the invention, one or more parameters such as age, sex, location (which may be expressed, e.g., in terms of political or geographic regions), and time may be used to calculate one or more reference ranges for an analyte. For example, one or more of these parameters may be used to select sub-populations of historical test results. One or more such selected sub-populations may then be subjected to statistical analysis, e.g., as is known in the art, to calculate respective reference ranges.

In an embodiment of the invention, reference ranges that have been calculated as above may be associated with the values of the parameters used to select the population. In such an embodiment, corresponding parameters may be recorded with a subsequent performance of test. Such parameters may be used to select a reference range most applicable to that performance, and that reference range may then be, e.g., reported along the with test result to a prescribing physician and/or used to help judge whether the test result indicates an abnormal medical condition, among other uses.

Returning to FIG. 3, in block 308, in an embodiment, it is determined whether the patient sample is pediatric or adult. In embodiments, separate processing flows may be invoked on the basis of this determination. Similarly, in embodiments, separate processing flows may be invoked on the basis of other demographic information, e.g., gender. For example, the system may fetch different reference ranges on the basis of these factors.

In block 310, according to embodiments, a quality control process is invoked. The quality control process may be used to calculate a grade for a test or batch of tests based on the expected distribution of test results for samples in the batch, factoring in the expected variations in individual result, ultimately avoiding false positives for samples that are within an adjusted reference range, but that otherwise may have been flagged as requiring re-testing.

In block 312, according to embodiments where offset values are fetched instead of reference ranges, the variation data in the form of offsets are applied to the known reference range. According to embodiments where the reference range fetched in block 306 already has the offset applied, block 312 may be circumvented.

In block 314, in an embodiment, a determination is made as to whether the patient sample is within the adjusted reference range. For example, if a normal or optimum 25 OH Vitamin D reference range is 25-80 ng/ml, but the adjusted reference range based on some factor, e.g., time of year, indicates a "normal" reference range of 5-50 ng/ml for that sample at that time, the system may determine that a sample of 5 ng/ml is within the reference range. The system, which would have otherwise flagged this sample as requiring further quality control or even re-testing, could be configured in an embodiment to not flag this sample as indicative of a quality issue. In another embodiment, such a determination could be held until multiple samples can be analyzed.

In block 316, in an embodiment, a report is generated. This report may include a grade, based on the quality control analysis, and/or information about the test, which may include some or all of, e.g., patient information, identification of the testing methodology, location, and/or apparatus, or one or more diagnosis codes. In an embodiment of the invention, the report may comprise identification of the measured analyte, the measured value, and the reference range selected and/or retrieved in block 306. The report as generated in block 316 may be tangible, e.g., written or printed on paper, or electronic, e.g., a representation of the reported information, linked together, in a computer memory and/or computer-readable storage medium.

In block 318, the system, in an embodiment, may be configured to release the sample or flag it for re-testing based on the quality control grade, or may hold the sample for further analysis based on an aggregate analysis of other samples taken immediately before and immediately after the sample, so that, for example, "drift" of a testing apparatus may be caught prior to releasing samples.

In block 320, the quality control grade or other results relating to the sample may be made available globally to the system or other systems, e.g., for use in the aggregate analysis discussed in the previous paragraph.

Figure 4:
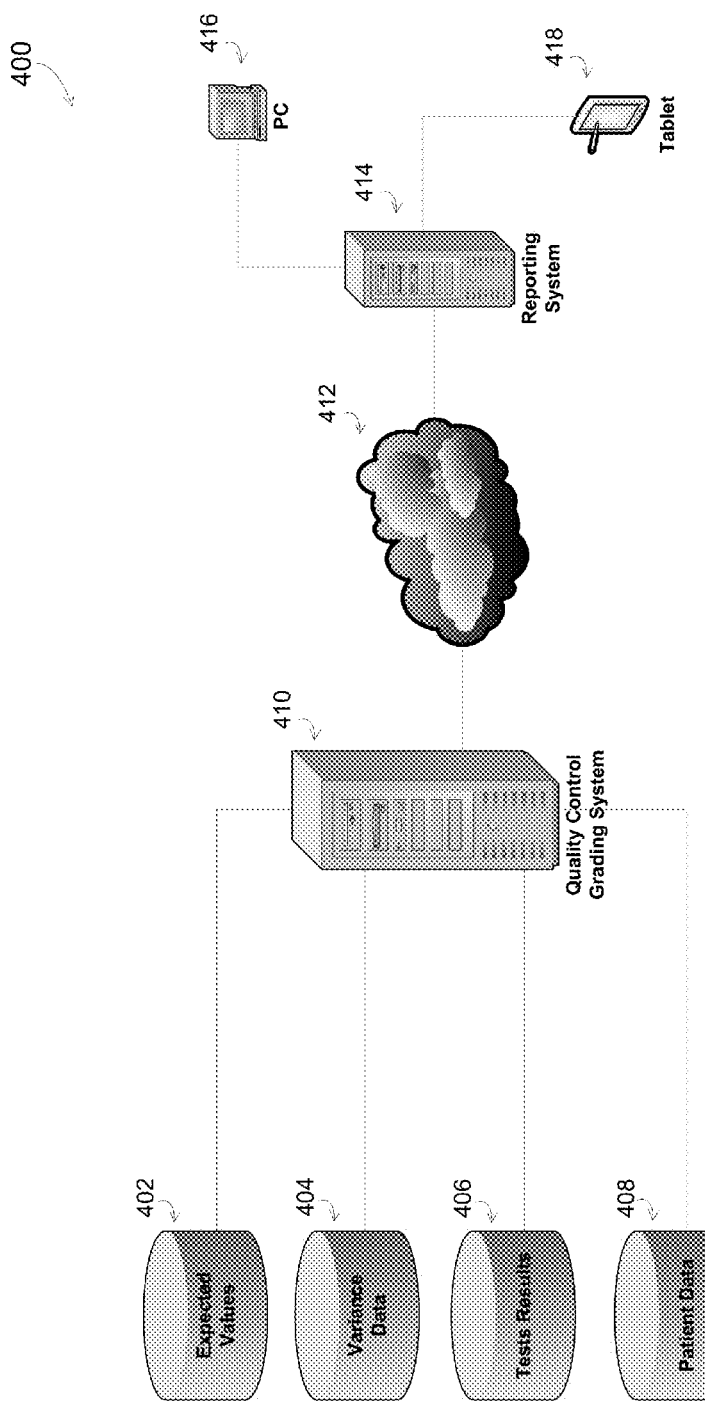
FIG. 4 is a system diagram depicting an exemplary system for calculating a grade for a test or batch of tests based on the expected distribution of test results for samples in the batch, factoring in variations.

FIG. 4 is a system diagram depicting an exemplary system for calculating a grade for a test or batch of tests based on the expected distribution of test results for samples in the batch, factoring in variations.

According to embodiments, databases 402, 404, 406, and 408 may store, respectively, expected values for a particular test or sample; variance data (offsets) or reference ranges for a particular test or sample; tests results of samples processed for quality control before and after the present sample; and patient data.

Server 410, in an embodiment, may be configured to store and process the calculations and algorithms for calculating a grade for a test or batch of tests based on the expected distribution of test results for samples in the batch, factoring in variations fetched from, e.g., variance data database 404.

Server 410, in embodiments, may communicate over network 412 with reporting system 414, and PC 416 and tablet 418. Reporting system 414 may be used, for example to distribute the report(s) generated in block 316 of FIG. 3.

The present invention has been illustrated and described with respect to specific embodiments thereof, which embodiments are merely illustrative of the principles of the invention and are not intended to be exclusive or otherwise limiting embodiments. Accordingly, although the above description of illustrative embodiments of the present invention, as well as various illustrative modifications and features thereof, provides many specificities, these enabling details should not be construed as limiting the scope of the invention, and it will be readily understood by those persons skilled in the art that the present invention is susceptible to many modifications, adaptations, variations, omissions, additions, and equivalent implementations without departing from this scope and without diminishing its attendant advantages. For instance, except to the extent necessary or inherent in the processes themselves, no particular order to steps or stages of methods or processes described in this disclosure, including the figures, is implied. In many cases the order of process steps may be varied, and various illustrative steps may be combined, altered, or omitted, without changing the purpose, effect or import of the methods described. It is further noted that the terms and expressions have been used as terms of description and not terms of limitation. There is no intention to use the terms or expressions to exclude any equivalents of features shown and described or portions thereof. Additionally, the present invention may be practiced without necessarily providing one or more of the advantages described herein or otherwise understood in view of the disclosure and/or that may be realized in some embodiments thereof. It is therefore intended that the present invention is not limited to the disclosed embodiments but should be defined in accordance with the claims that follow.

I claim:

1. A method of measuring respective values of an analyte in each of a plurality of samples of biological material, each sample being obtained at a respective time on a respective date from a respective one of a plurality of patients, the method being performed by a computer system that comprises one or more processors, one or more computer-readable storage media operatively coupled to at least one of the processors, and one or more interfaces operatively coupled to at least one of the processors, and the method comprising:

receiving through at least one of the interfaces a plurality of prior values, each prior value being a measurement of a respective value of the analyte in a respective member of a population comprising a plurality of individuals;

dividing the population into a plurality of subpopulations by applying one or more criteria to the plurality of individuals, each subpopulation comprising a plurality of the plurality of individuals;

associating each of the prior values with a respective one of the subpopulations by applying the one or more criteria to the respective individual in whom the respective prior value was measured;

for each subpopulation, determining that a statistical property of the prior values associated with that subpopulation varies according to a time-periodic function, the time-periodic function being a mathematical function such that for all times t and a fixed time interval T, the value of the function at time t equals the value of the function at time t+T;

subdividing the interval T into a plurality of subintervals;

for each subpopulation and for each subinterval, based on the determined variation of the statistical property of the prior values associated with that subpopulation, calculating a reference range for the analyte that applies to the subpopulation and the subinterval;

receiving through at least one of the interfaces a plurality of values, each value being a measurement of the analyte in a respective one of the plurality of samples, the values representing respective results of an assay performed on the samples as a batch;

for each sample, determining that the sample was obtained within a particular subinterval and that the patient from whom the sample was obtained is a member of a respective subpopulation;

for each sample, identifying an applicable reference range of values based on the subinterval within which the sample was obtained and the subpopulation of which the patient from whom the sample was obtained is a member;

calculating a single quality-control grade for the batch as a whole based on, for each sample, comparing the respective measured value with the respective applicable reference range for that sample; and based on the quality-control grade, determining to do exactly one of: 1) releasing the values for diagnostic use, and 2) repeating the assay on the samples.

2. The method of claim 1, wherein each sub-population comprises a plurality of persons other than the plurality of patients.

3. The method of claim 2, wherein:

the sub-populations are defined by dividing a larger population according to criteria that include age; and for each sample, the applied reference range is selected based on the age of the patient from whom the sample was obtained.

4. The method of claim 2, wherein:

the sub-populations are defined by dividing a larger population according to criteria that include sex; and for each sample, the applied reference range is selected based on the sex of the patient from whom the sample was obtained.

5. The method of claim 2, wherein:

the sub-populations are defined by dividing a larger population according to criteria that include location; and for each sample, the applied reference range is selected based on the location of the patient from whom the sample was obtained.

6. The method of claim 2, comprising, for each sub-population and temporal range, calculating a respective mean value for the analyte;

wherein calculating the reference range for application to the sub-population as a whole and the temporal range comprises using the respective mean value associated with the sub-population and the temporal range.

7. The method of claim 6, comprising, for each-sub-population and temporal range, calculating a respective standard deviation of the values within the sub-population and associated with the temporal range;

wherein the reference range for application to the sub-population as a whole and the temporal range is the range of values within two respective standard deviations of the respective mean value.

8. The method of claim 1, comprising:

based on the quality-control grade, determining to repeat the assay on the samples; and performing the assay a second time on each of the samples.

* * * * *